United States Patent
Tacke et al.

(10) Patent No.: US 6,555,820 B1
(45) Date of Patent: Apr. 29, 2003

(54) PHOTOMETRIC DEVICE AND PHOTOMETRIC METHOD FOR DETERMINING THE GROSS CALORIFIC VALUE OF A TEST GAS

(75) Inventors: Maurus Tacke, Freiburg (DE); Joachim Kastner, Dortmund (DE)

(73) Assignee: Flow Comp Systemtechnik GmbH, Dortmund (DE)

( * ) Notice: Subject to any disclaimer, the term of this patent is extended or adjusted under 35 U.S.C. 154(b) by 0 days.

(21) Appl. No.: 09/763,448

(22) PCT Filed: Aug. 21, 1999

(86) PCT No.: PCT/DE99/02627

§ 371 (c)(1),
(2), (4) Date: Feb. 23, 2001

(87) PCT Pub. No.: WO00/11452

PCT Pub. Date: Mar. 2, 2000

(30) Foreign Application Priority Data

Aug. 24, 1998 (DE) ................................ 198 38 301

(51) Int. Cl.[7] ............................................... G01N 21/35
(52) U.S. Cl. ........................ 250/339.01; 250/339.02; 250/339.07; 250/339.12; 250/339.13
(58) Field of Search ................... 250/339.01, 339.02, 250/339.07, 339.12, 339.13

(56) References Cited

U.S. PATENT DOCUMENTS

| | | |
|---|---|---|
| 4,553,032 A | 11/1985 | Lo et al. |
| 4,594,510 A | 6/1986 | Brown et al. |
| 4,800,279 A | 1/1989 | Hieftje et al. |
| 6,157,455 A | * 12/2000 | Pinvidic et al. ............. 356/437 |

FOREIGN PATENT DOCUMENTS

| | | |
|---|---|---|
| DE | 2635769 | 9/1977 |
| WO | 9832003 | 7/1998 |

* cited by examiner

Primary Examiner—Constantine Hannaher
(74) Attorney, Agent, or Firm—Stevens, Davis, Miller & Mosher, LLP

(57) ABSTRACT

A photometric device and method for determining the gross calorific value of a test gas, especially natural gas having a radiation source that produces a measuring beam and a modulation unit to modulate the measuring beam. A test cell with test gas and a receiver for the beam are arranged successively in the path of the measuring beam. The measuring signals of the receiver are supplied to an evaluation unit that includes at least one signal amplifier for the amplification of the signals. The signal amplifier is provided with adjustment devices to adjust the signal amplifier according the spectral properties of the measuring beam. The gross calorific value of the gas is indicated by the sum of the amplified measuring signals produced in a computing machine.

21 Claims, 2 Drawing Sheets

Figure 1:
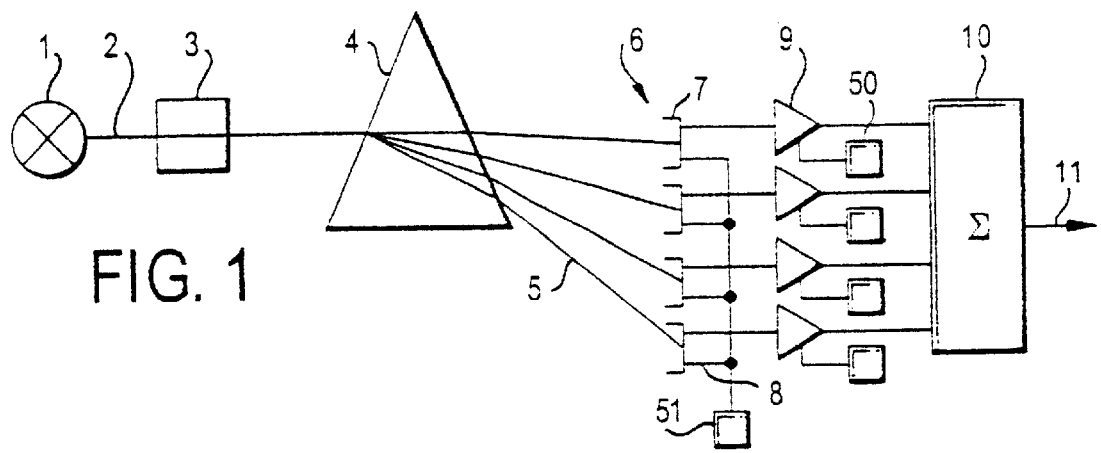

PHOTOMETRIC DEVICE AND PHOTOMETRIC METHOD FOR DETERMINING THE GROSS CALORIFIC VALUE OF A TEST GAS

The invention relates to a photometric device for determining the gross calorific value of a test gas with a radiation source that generates a measuring beam and a spectral unit for dividing the measuring beam spectrally, with a test cell for the absorption of the test gas and a radiation receiver, which generates electric measuring signals in dependence on the measuring beam intensity and which is electrically connected with an evaluation unit that is equipped with at least one signal amplifier for amplification of the measuring signals, being arranged successively in the path of the measuring beam.

The invention furthermore relates to a method for the photometric determination of the gross calorific value of a test gas, in which a test cell that is filled with test gas is interspersed with the measuring beam, in which the measuring beam intensity that is permitted to penetrate by the test cell is measured with the help of a radiation receiver that generates measuring signals, in which the measuring signals are generated in relation to appropriate measuring signals without test gas in the test cell and spectral absorption values that are allocated to wave ranges are generated, and in which the allocated spectral absorption values are amplified with the help of at least one signal amplifier.

From U.S. Pat. No. 4,594,510 we know of a photometric device and a method for determining the gross calorific value of a test gas that is equipped both with a radiation source that generates a measuring beam and a spectral unit for dividing the measuring beam spectrally. A test cell for the intake of the test gas and a radiation receiver are arranged in the path of the measuring beam. With the radiation receiver, electric measuring signals can be generated in dependence on the measuring beam's intensity. The radiation receiver is electrically connected with an evaluation unit, which is equipped with at least one signal amplifier for the amplification of the measuring signals. In order to determine the gross calorific value of test gases whose material composition is not known, a calibration must first be performed during which the gross calorific values of calibrating gases, which contains at least as many material components as the test gas of unknown composition, are determined. Since the exact material composition of the test gas is inherently not known, in practice the calibration is generally performed with considerably more material components in the calibrating gases than would theoretically be required. For sufficient accuracy of the determination of the gross calorific value, it is furthermore necessary that when determining the proportionality factors for amplifying the measuring signals the spectral support areas are selected under the assumption of a certain, very likely accurate material composition of the test gas in order to record the material components adequately. In practice, it showed that sufficiently exact determinations of gross calorific values of test gases with different origins, and therefore with different material compositions, are very complex.

From DE-A-48 00 279 we know, with regard to the methods and devices for the determination of physical properties of samples in the short-range infrared spectral region, that a Fourier transform spectrometer is used.

In the report by H. M. Heise entitled "Infrarotspektrometrische Gasanalyse" (Infrared Spectrometric Gas Analysis) from the publication "Infrarotspektroskopie" (Infrared Spectroscopy), issued by H. Güunzler, Springer-Verlag, Heidelberg, Germany 1996, both dispersive and non-dispersive methods and spectrometers are revealed for performing these methods. While a dispersive device is equipped with a dispersive element such as a grating for the spatial splitting of infrared radiation in dependence on its wavelength, the revealed non-dispersive devices are, for example, equipped with a filter device for selecting a wavelength.

The gross calorific value of a gas creates a connection between the gas volume consumed during combustion and the amount of heat produced during the same and has achieved great importance for the control engineering of natural gas operated equipment, for example. Among gas mixtures such as natural gas, the gross calorific value is dependent upon the composition of the gas mixture. When purchasing natural gas, the gas volume is generally used as the basis for calculating the purchase price, with the gas gross calorific value affecting the purchase deal directly. Therefore, a volume-related purchase price assumes information about the gross calorific value of the gas intended to be purchased in order to justify a higher purchase price for gases with high gross calorific value over less expensive offers.

Due to the ongoing liberalization of the energy market, which is associated with the decline of regional energy monopolies, natural gases of various providers and composition will be fed through joint pipeline systems in the near future. The quality of the natural gas used by an end user from the pipeline system is therefore not known until it is consumed so that problems with regard to volume-related purchase price billing can occur. It would, therefore, be desirable to have a method and a device that would allow a determination process of the gross calorific value of a gas, for example when removing it from the pipeline system, that is quick and requires few metrology efforts. This way, calculating the cost on the amount of heat achieved with the gas is possible without the provider knowing the gas that is used or its exact composition.

Direct measurement of the gross calorific value of a gas is generally performed with calorimeters. For this, a specified volume of the test gas is burned, and the thermal energy released thereupon to a defined quantity of a coolant medium is measured by the temperature increase of the coolant medium. Suitable coolant media are for, example, air or water. While the high degree of inertia of the measurement proves disadvantageous for the quick recording of the gross calorific value of a natural gas, despite its high degree of accuracy when utilizing water, the disadvantages for utilizing air as a coolant medium lie especially in the complicated mechanics for setting a certain quantitative proportion of gas, combustion air and cooling air.

We furthermore know of cost-intensive calorimeters based on stoichiometric combustion, where a certain air requirement that is needed for the combustion of a defined quantity of the test gas is determined.

One method for determining the gross calorific value indirectly involves gas chromatography, in which the gas composition is determined quantitatively and the gross calorific value of the overall gas mixture is calculated based on knowledge of the gross calorific values of the individual components. The disadvantages of gas chromatography are the high procurement costs of the necessary devices as well as the personnel qualifications required for their operation.

Compared to gas chromatography, previously-known methods for determining the gross calorific value place fewer demands on the types of devices required to perform the method and have the benefit of a shorter measuring time, especially in comparison with the calorimetric method. For this method, an absorption spectrum of the natural gas is measured in the short-range or medium-range infrared spectral region, which is composed cumulatively of the sum of the individual spectra of the gas components present in the gas, and analyzed with the help of suitable spectral analysis methods. The percentage of absorbance of a component from the overall spectrum thus determined is equal to the concentration percentage of this component in the test gas. Thereafter, based on knowledge of the respective gross calorific value of the components, the gross calorific value of the entire gas mixture is calculated. The spectral analysis, however, is difficult due to heavy overlapping of the absorption bands of different gas components, often leads to inaccurate results and requires a very high degree of computation.

The invention is therefore based on the task of further developing a device and a method of the kind described above in such a way that the gross calorific value, even of a test gas with an unknown material composition, can be determined quickly, simply, inexpensively and reliably.

In a device in accordance with the invention the task is resolved by being able to determine—from the composition of the test gas with regard to the components or functional groups and the position of absorption bands and absorption lines—independent partial spectral regions of an absorption band and/or a spectral region comprising absorption lines, by being able to amplify—with the or every signal amplifier that is allocated to the partial spectral region—the measuring signal coming from this partial spectral region with a degree of amplification that is allocated to this partial spectral region, and by the fact that the evaluation unit comprises a summer for summing up the amplified measuring signals.

In the method, the task is resolved in accordance with the invention by being able to determine—from the composition of the test gas with regard to the components or functional groups and the position of absorption bands and absorption lines—independent partial spectral regions of an absorption band and/or a spectral region comprising absorption lines, by being able to amplify—with the or every signal amplifier that is allocated to the partial spectral region—the measuring signal coming from this partial spectral region with a degree of amplification that is allocated to this partial spectral region, and by the fact that the amplified measuring signals are added for the calculation of the gross calorific value of the test gas.

The reaction heat generated during gas combustion is based on the oxidation of C—H bonds, with the thermal quantity that is generated being dependent upon the respective bond energy. The invention is based on the idea that the oscillations of the C—H bonds, which have among each other the same defined bonding energy and generate the same amount of heat during combustion, interact with electromagnetic radiation at an allocated wavelength. Based on this prerequisite, the gross calorific value of the gas can be calculated from wavelength-dissolved measurements in fixed partial spectral regions independent on the material composition of the test gases and from a weighting of the integral spectral absorption values of these partial spectral regions. The allocation of the C—H oscillations to a defined previously-known component of the gas is therefore only required within the framework of additional corrective procedures at best so that an often inaccurate, comprehensive spectral analysis can be avoided.

In a useful development of the invented device, the evaluation unit is an electric circuit, and for the purpose of adjusting the degrees of amplification one or more adjustable control voltage sources, whose respective electric voltage controls the amplification degree of the allocated signal amplifier, are incorporated.

In one variant version, the evaluation unit is a digital computing device that is equipped with a sum memory, with means of adjustment with an amplification parameter memory for storing amplification parameters that are allocated to the respective partial spectral regions being incorporated for adjusting the amplification degrees, with the signal amplification being conducted by multiplying the measuring signals—through a central processing unit of the computing device—with the amplification parameters in dependence on the spectral property of the measuring beam generating the measuring signal.

In an advantageous version, the photometric device is equipped with a dispersive element as the spectral unit for the purpose of spatial splitting of the measuring beam in dependence on its wavelength and also with a detector row as the radiation receiver with detector elements that are arranged next to each other, with each detector element being connected to a signal amplifier, respectively. In such a design where the device is further developed, the dispersive element is a diffraction grating.

In a variant further development, the invented photometric device comprises a spectral switch unit for selecting the partial spectral regions of the measuring beam and a detector element as radiation receiver, with means of adjustment, which are coupled with the spectral switch unit and with which the amplification degrees can be adjusted, being incorporated. In such a development, the spectral switch unit is a filter wheel with spectral filters, triggered by a filter wheel drive.

In another useful further development, the spectral unit is an interferometer, which is equipped with a beam splitter for splitting the measuring beam into two optical paths, which are limited by a stationary mirror or a mirror that can be moved with a control element. The mirrors are aligned in such a way that the portions of the measuring beam reflected from them unite in a joint beam path. Beyond that, the control element is coupled with means of adjustment, with which the amplification degrees can be set.

In a preferred version, the radiation source is an infrared radiation source generating infrared radiation in the medium-range infrared spectral region and the radiation receiver is a sensitive radiation receiver in the medium-range infrared spectral region.

In a version deviating from this one, the radiation source is an infrared radiation source generating infrared radiation in the short-range infrared spectral region and the radiation receiver is a sensitive radiation receiver in the short-range infrared spectral region.

In a useful further development, the invented device is equipped with a spectral accumulator, with which the measuring signals can be stored in pairs with the respectively allocated partial spectral regions.

In a preferred design of the invented method, the measuring beam is split spatially in dependence on its wavelength.

In a version deviating from this one, the invented method involves the modulation of the amplitude of the measuring beam with the help of an interferometer.

In a beneficial version, the spectral absorption values are amplified with allocated partial spectral regions from the spectral region of the C—H oscillation, and particularly from the range between 3 $\mu$m and 4 $\mu$m.

In a version deviating from this one, the spectral absorption values are amplified with allocated partial spectral regions from the spectral region of the C—H harmonic oscillation, and particularly from the range between 1.5 μm and 2 μm.

It is useful to check the test gas for at least one interfering foreign gas, whose spectral absorption values are known in dependence on the wavelength and which does not contribute to the gross calorific value, by measuring characteristic spectral absorption values with established partial spectral regions, to determine the percentage of the foreign gas in the test gas in dependence on the characteristic spectral absorption values and to subtract the percentage of the foreign gas interfering with the measurement from the measured spectral absorption values.

In a beneficial version, the test gas is examined for special gases contributing to the gross calorific value by measuring characteristic spectral absorption values at established wavelengths; these gases differ from a main component of the test gas based on their chemical composition or structure, such as due to additional functional groups or branching of hydrocarbon chains.

In a beneficial version, the partial spectral regions of allocated spectral absorption values are stored as a spectrum in the spectral accumulator.

Figure 2:
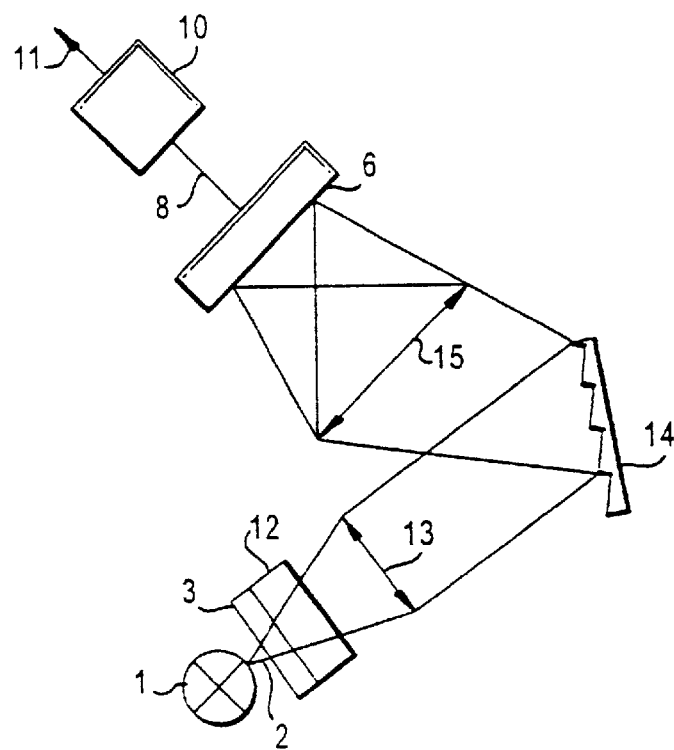
Figure 3:
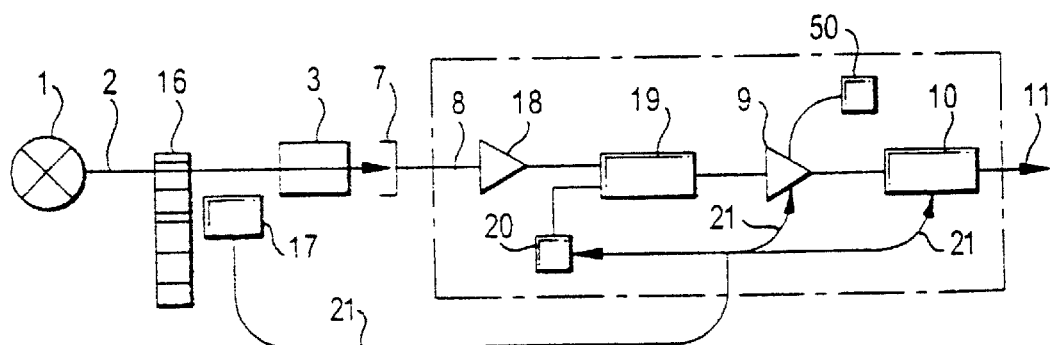
Figure 4:
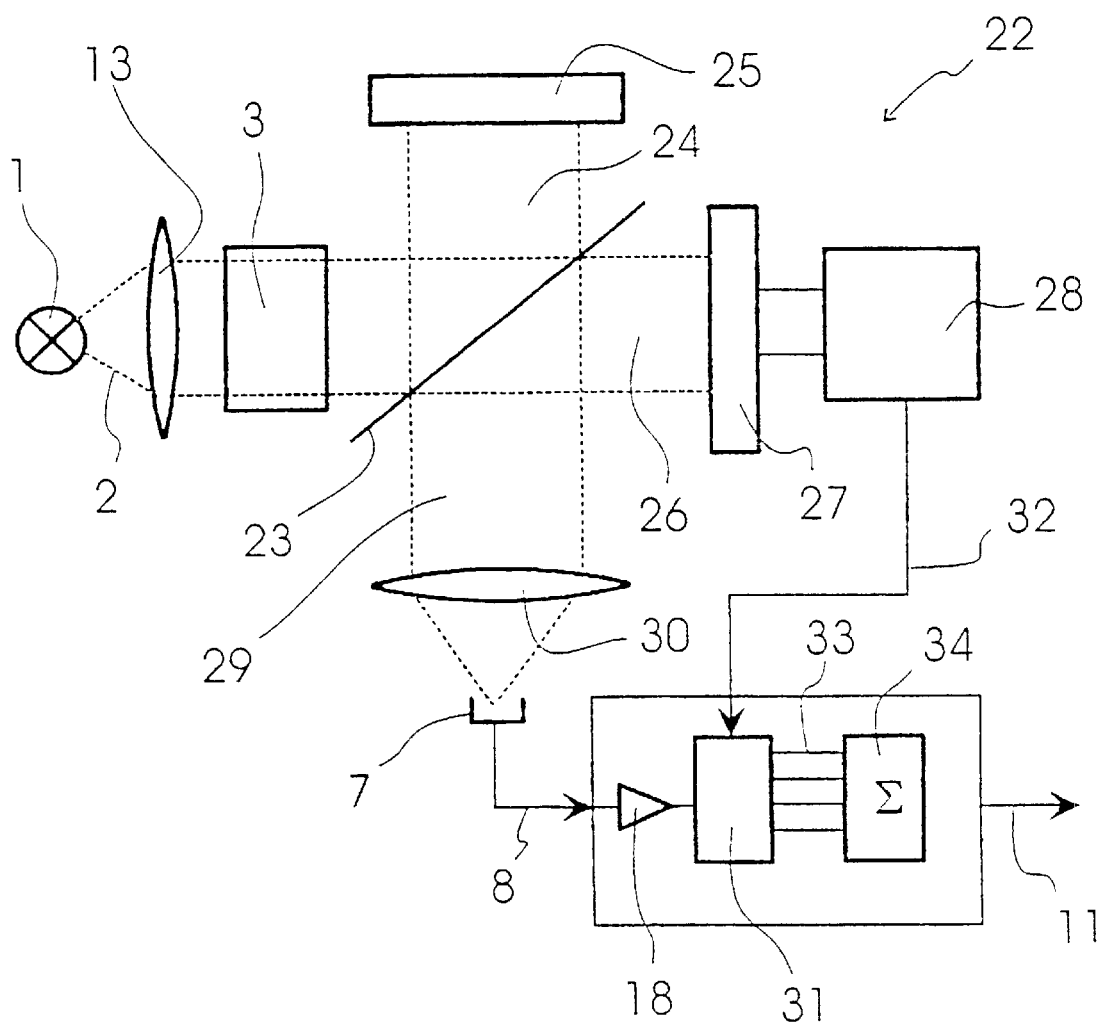

Additional useful versions and advantages of the invention are the subject of the following description of examples in accordance with the invention with reference to the figures in the drawing. They show:

FIG. 1 a diagrammatic view of one version of the invented photometric device with a prism, FIG. 2 the photometric device in accordance with FIG. 1 with a grid, FIG. 3 the photometric device in accordance with FIG. 1 with a filter wheel for switching infrared radiation and FIG. 4 the device based on the invention in accordance with FIG. 1 with an interferometer.

FIG. 1 shows a diagrammatic view of one version of the invented device. Broadband infrared radiation 2, which covers the medium-range infrared spectral region from 3 μm to 12 μm and which is generated as a measuring beam by a radiation source 1, spreads in the test cell 3 filled with test gas and subsequently encounters a prism 4 that is arranged behind the test cell 3 as the dispersive element. The prism 4 causes the broadband infrared radiation 2 to be split spatially in dependence on its wavelength. This splitting process is depicted more closely in FIG. 1 with the partial radiation 5 propagating in a fan-like manner, of which only four are shown for clarity reasons, however whose quantity is 10 in a simple version of rough spectral resolution.

A detector row 6 with detector elements 7 that are located next to each other is arranged in the path of some of the partial radiation 5 in such a way that each detector element 7 is allocated to a certain, previously specified partial beam 5 and thus a wave range with an established width and an established medium-range wavelength. The spectral width of the infrared radiation 2 detected by a detector element 7 is dependent upon the resolution of the photometric device.

Rotating the prism 4 enables the spectral region utilized for the measurement process to be selected. In the version shown, the prism 4 is aligned in such a way with regard to the incident infrared radiation 2 that the detector elements 7 cover a spectral range of 3.2 μm to 3.6 μm. The infrared radiation 2 of this spectral region is absorbed by the oscillations of the C—H bonds of the test gas. In a variant version, the wavelengths of the broadband infrared radiation 2 are within the short-range infrared spectral region, with the prism 4 being aligned in such a way with regard to the infrared radiation 2 that the detector elements 7 cover a wave range between 1.6 μm and 1.8 μm. The absorption bands of the first harmonic oscillation of the C—H bond are within this spectral region. Although compared to the basic oscillation absorption of the harmonic oscillation of the C—H bonds is weaker, the short-range infrared spectral region offers advantages over the medium-range infrared spectral region when it comes to metrology requirements. The detector elements 7, respectively, comprise an electronic circuit (not shown), which normalizes the respective measuring signal to a measuring signal that is obtained without test gas for the purpose of generating a spectral absorption $\alpha_{\lambda,i}$ with an allocated wavelength $\lambda_i$ and subsequently logarithmizes the standardized measuring signal electronically. The spectral absorption values or test interaction degrees obtained this way are fed via measuring signal lines to a signal amplifier 9, whose degree of amplification is adjusted -by feeding a control voltage with the help of control voltage sources 50—in such a way that it corresponds to a spectral gross calorific value parameter $b\lambda_i$ with an allocated wavelength $\lambda_i$. For this, the set spectral gross calorific value parameter $b_{\lambda,i}$, respectively, is selected in reference to the spectral width and the medium-range wavelength $\lambda_i$ of the infrared radiation, which is recorded by the respectively allocated detector element 7.

The spectral gross calorific values $\alpha_{\lambda,i} \cdot b_{\lambda,i}$ generated by the amplification process and dispersed across the absorption spectrum are subsequently added in a sum memory, which in this version is designed as a summer 10, so that its output signal 11 corresponds to the gross calorific value of the test gas. The output signal is subsequently fed to the output unit (not shown), such as a digital display panel, which indicates the calculated gross calorific value of the test gas to the operator. Amplification and adding of measured spectral absorption in the summer 10 for the purpose of calculating the gross calorific value (B) can be depicted with the formula $$B = \Sigma_i \alpha_{\lambda,i} \cdot b_{\lambda,i} \quad (1)$$

The set of spectral gross calorific value parameters $b_{\lambda,i}$ required for setting the signal amplifier 9 is of decisive importance for determining the gross calorific value (B) of the test gas. Apart from the allocated wavelength $\lambda_i$, the spectral gross calorific parameters $b_{\lambda,i}$ are dependent upon the width of the respectively detected spectral region. A reduction in the number of detector elements 7 that are arranged in the detector row 6 must therefore lead to a reduction in the number of support areas that are available throughout the observed spectral region of 3.2 μm to 3.6 μm and generally to a widening of the spectral region detected by each detector element 7. These influencing variables must be taken into consideration when determining the spectral gross calorific value parameters, e.g., with numerical computation methods by adjusting the preliminary results of the numerical method to the respectively employed photometric device with appropriately selected adjusting parameters. It is useful to determine a set of spectral gross calorific value parameters $b_{\lambda,i}$ empirically, for which one or several test gases with known gross calorific values and known composition are examined and the spectral gross calorific parameters $b_{\lambda,i}$ are changed until the determined gross calorific value agrees with the previously-known gross calorific value.

In order to determine a set of spectral gross calorific values, the spectral gross calorific value parameter $b_{\lambda,i}$ is developed, for example, in accordance with $$b_{\lambda,i} = r + s/\lambda_i + t/\lambda_i^2 + \quad (2)$$

wherein r, s and t are parameters. Adding further links increases the accuracy of the calibration. However, it is sufficient for most applications to stop after the second link. For the calibration, the spectral absorption $\alpha_{\lambda,i}$ of the calibration gases and calibration gas mixtures with the known gross calorific value $B_{Bek}$ [$B_{known}$] is measured. By inserting equation (2) into equation (1), a calculated or measured gross calorific value B is computed from the respectively measured set of spectral absorption $\alpha_{\lambda,i}$ and from as appropriately as possible selected initial values of the adjusting parameters r, s, t . . . With the help of a common adjusting method, for example, based on the smallest error squares, the adjusting parameters are then changed until the sum of deviations from the calculated gross calorific value B of the known gross calorific value $B_{Bek}$ reaches a minimum. When performing the calibrating measurement, it should be ensured that the employed calibration gas mixtures do not result in linear combinations from each other.

The evaluation unit of the example shown in FIG. 1 comprises all electric circuits that process the signal generated by the detector row 6, and particularly the signal amplifier 9, the control voltage sources 50 as well as the summer 10. Deviating from this example, the invented evaluation unit can also take on the design of a suitably-equipped computing device. For this, the detector elements 7 of the detector row 6 are connected with a multi-purpose card (not shown) of the computing device via the measuring signal line 8. Furthermore, a measurement program of the computing device, which is provided for controlling the evaluation procedure, instructs a central processing unit (CPU) of the computing device to multiply the measuring signals digitized by the multi-purpose card with allocated spectral gross calorific value parameters for the purpose of amplification. The spectral gross calorific value parameters required for this have been stored in an amplification parameter register. Subsequently, the control program instructs the computing device to calculate the sum of these products and thus the gross calorific value of the gas.

Small foreign particles contained in the test gas, such as carbon dioxide, which contribute to the measured absorption but do not contain any oxidizable C—H bonds that contribute to the gross calorific value, interfere with the calculation of the gross calorific value. In order to recognize the absorption of such small foreign particles and reduce their influence on the determined gross calorific value, the spectrum of the test gas is recorded between 3 $\mu$m and 12 $\mu$m For this, the prism 4 is rotated by a prism drive (not shown). The prism drive is equipped with an angle sensor, which generates electric signals in dependence on the angle position of the prism and thus in dependence on a medium-range wavelength recorded by a certain detector element 7. The established detector element 7 and the angle sensor are connected with a memory unit 51 which stores the received signals in pairs as spectrum.

The spectrum stored in the accumulator is then checked for characteristic absorption bands of foreign particles. For this, a spectral analysis program, for example, accesses a reference accumulator in which a series of different reference spectra of foreign particles are stored. When the spectral analysis program recognizes characteristic absorption bands of a foreign particle based on a comparison of the measured spectrum with the reference spectrum, it deducts such a percentage of the reference spectrum from the overall measured absorption spectrum that the characteristic absorption bands can no longer be recognized.

In accordance with the invention, the spectral region in which the test gas is measured can go beyond the medium-range infrared spectral region because—although the foreign particles experience considerable absorption in the infrared—the characteristic bands required for the allocation are located, for example, in the short-range infrared or visible spectral region. For this it may be necessary to replace the wavelength-dependent components shown in FIG. 1, such as the radiation source 1 and the detector row 6, with components that are suited for utilization in a different wave range.

Beyond that, the spectral information can be utilized for making suitable spectral gross calorific value parameters of special molecules available, which contain C—H bonds that contribute to the gross calorific value, but differ from generally expected molecules based on their structure or composition. For example, molecules such as cyclohexane, aromatic compounds or methyl iodide have a chemical composition or structure that deviates from those gases mainly contained in natural gas, such as methane or ethane. The chemically differing structure of such special molecules generally changes the absorption behavior of the C—H bonds and can lead to the fact that their percentage on the gross calorific value is not recorded. The contribution of special molecules to the gross calorific value of a gas may need to be taken into consideration in order to avoid inaccurate measurements.

The absorption of special molecules is therefore taken into consideration in an additional method of approximation. Here, the spectrum is examined throughout the entire spectral region, which can go beyond the medium-range infrared spectral region, for characteristic absorption in the same manner as that already described in connection with the detection of foreign particles; the absorption can be recognized as described above with a spectral analysis program by comparing it to reference spectra.

The respectively recognized molecules are allocated a parameter set $b_{1, \lambda i, \lambda j}$, which is stored in an auxiliary parameter memory. The additional contribution $B_1$ of the special molecule to the gross calorific value is computed based on $$B_1 = \Sigma_i \alpha_{\lambda,i} \cdot \Sigma_j \alpha_{\lambda,j} \cdot b_{1,\lambda i,\lambda j} = \Sigma_{ij\alpha\lambda i} \cdot \alpha_{\lambda,j} \cdot b_{1,\lambda i,\lambda j}, \qquad (3)$$

wherein the summation over j corresponds to the accumulating scanning of support areas $\lambda j$ within a spectral region, which is offset spectrally compared to the original spectral region allocated to $\lambda i$. The parameter set $b_{1,\lambda i, \lambda j}$ can be obtained with a suited calibration method. The additional gross calorific value $B_1$ obtained with this additional method is added to the gross calorific value B in order to compute the overall gross calorific value $B_{ges}$ [$B_{total}$] of the gas.

FIG. 2 shows a photometric device in accordance with FIG. 1 with a clearly-depicted beam path. The radiation source 1 generates the broadband infrared radiation 2, which encounters a diffraction grid via an image lens 12 and a collimator 13 as a parallel beam and is split by this grid spatially in dependence on the wavelength. The diffraction grid 14 has the design of a reflection grating so that spatially split infrared radiation 2 is reflected and subsequently encounters a lens 15, which focuses the split beam onto the detector row 6. The detector row 6 in turn consists of detector elements that are arranged next to each other (not shown). Due to the spatial splitting of the beam, each detector element records a certain spectral region of the infrared radiation 2 and is amplified in dependence on the spectral position as well as the spectral width of this radiation by signal amplifiers (not shown). The degree of amplification of the signal amplifier has been adjusted in such a way that it corresponds to a spectral gross calorific value parameter $b_{\lambda i}$. The spectral gross calorific values $\alpha_{\lambda i} \cdot b_{\lambda i}$ are then added in the summer 10 and result in the gross calorific value of the test gas as output signal 11.

FIG. 3 shows a version of the invented device with a filter wheel 16 as the switch unit for switching the wavelength of the infrared radiation 2. The filter wheel 16 is equipped with filters that are vertically aligned with the infrared radiation 2 and transmit only a certain spectral region of the broadband infrared radiation so that a wavelength or a wave range can be selected for the respective measurement process by rotating the filter wheel 16 via a filter wheel drive 17. The filter wheel drive 17 is equipped with a position transmitter, which generates signals in dependence on the filter position.

In the path of the filtered infrared radiation 2, the detector element 7, which generates an electric measuring signal in dependence on the infrared rays' intensity, is incorporated behind the test cell 3. The measuring signal is fed via the measuring signal line 8 to a pre-amplifier 18 for amplifying the measuring signal independent from the wavelength, and the pre-amplified measuring signal is then divided by a reference signal, which was recorded in the same position of the filter wheel 16 and stored in the reference memory 20. In order to allocate the pre-amplified measuring signal to the reference signal that was recorded at the appropriate wavelength, the reference memory 20 is electrically connected with the position transmitter of the filter wheel 17 via the position line 21. The measuring signal, which was normalized in the subtracting circuit 19, is then electronically logarithmized in order to generate an absorption signal and is fed to the signal amplifier 9, which in turn is connected with the position transmitter of the filter wheel drive 17 via the position line 21.

When the filter wheel drive 17 by rotating the filter wheel 16 changes the spectral region of the infrared radiation 2 used for measuring the absorption, the position transmitter of the filter wheel drive 17 generates an electric signal that is allocated to this new position, which causes the means of adjustment 50 of the signal amplifier 9 to adjust for example the degree of amplification of the signal amplifier 9, which can be adjusted through the control voltage, to the measurement conditions in such a way that it corresponds to a spectral gross calorific value parameter $b_{\lambda i}$ and that the absorption signal, which has now been amplified in dependence on the wavelength, corresponds to a spectral gross calorific value $\alpha_{\lambda i} \cdot b_{\lambda i}$. The spectral gross calorific values are added in the summer 10.

It is useful to select the filters that are arranged in the filter wheel 16 in such a way that upon rotation of the filter wheel 16 by 360 degrees it scans a spectral region of 3 µm to 12 µm. Upon full rotation of the filter wheel 16, the summer 10 is instructed by the position transmitter of the filter wheel drive 17 via the position line 21 to issue the appropriate gross calorific value of the test gas via the output signal 11 to a display unit (not shown).

FIG. 4 depicts a version of the invented photometric device with an interferometer 22 as the modulation unit. The interferometer 22, which is located behind the collimator 13 and the test cell 3, comprises a beam splitter 23 for splitting the infrared radiation 2 to an optical path 24, which is limited by a stationary mirror 25, and an optical path 26, which is limited by a moveable mirror 27. The moveable mirror 27 is connected with a control element 28 for the purpose of modulating the infrared radiation 2. Movement of the control element 28 occurs, for example, based on the principle of an electrodynamic loudspeaker.

In the optical paths 24, 26 the infrared radiation parts are reflected back by both mirrors 25 and 27 so that they overlap in a joint overlapping beam path 29. The radiation fields interfering with each other are focused with a suitable lens 30 onto the detector element 7, which generates an electric measuring signal, which in turn is fed to the pre-amplifier 18 via the measuring signal line 8 for the purpose of pre-amplifying the measuring signal independent of the wavelength.

The signal, which is measured in dependence on the position of the moveable mirror 27, corresponds to a Fourier transform of the spectrum of the infrared radiation 2. The pre-amplified measuring signal is split into elementary frequency ranges in an electronic filter 31, which is connected with the control element 28 via a coupling line 32. This splitting process that is performed in dependence on the position of the moveable mirror 27 corresponds to an electronic Fourier transform and in turn provides wavelength-dependent absorption signals as test interaction signals, which are fed via absorption signal lines 33 to a circuit 34, which amplifies the absorption signals in dependence on the frequency or wavelength and on the spectral resolution achievable in the measurement and adds the amplified spectral gross calorific values ($\alpha_{\lambda i} \cdot b_{\lambda i}$ thus obtained in dependence on the wavelength in a summer in order to then issue the output signal 11 to a display unit (not shown).

The evaluation units of the examples of the invention shown in FIG. 2 through FIG. 4 correspond to an electronic circuit. As was explained with regard to FIG. 1, the electronic evaluation unit can be replaced in accordance with the invention with digital electronics, such as digital signal processors or a computing device. The corrective measures described in connection with the version in FIG. 1, involving the consideration of small foreign particles and special molecules, can also be applied to the other versions described.

Furthermore it is feasible to perform measurements at various pressures and temperatures, with an appropriate set of spectral gross calorific value parameters being made available for each temperature or pressure.

What is claimed is:

1. Photometric device for determining the gross calorific value of a test gas having:

a radiation source (1) that generates a measuring beam (2);

a spectral unit (4, 14, 16, 22) for dividing the measuring beam (2) spectrally into a plurality of adjacent partial spectral regions of a spectral region having several absorption bands comprising absorption lines;

a test cell (3) for containing the test gas arranged in the path of said measuring beam;

a radiation receiver (6, 7), for generating electric measuring signals in dependence on the measuring beam intensity in their respective partial spectral region, and is arranged in the path of said measuring beam, wherein the measuring signals relate to the partial spectral regions of the spectral region having several absorption bands; and an evaluation unit electronically connected to the radiation receiver and equipped with at least one signal amplifier (9, 34) for amplification of the measuring signals, wherein based upon a composition of the test gas with regard to the components or functional groups of the test gas and positions of the absorption bands and the absorption lines, the radiation receiver records independent partial spectral regions of a said absorption band and/or a said spectral region comprising the absorption lines creating one of said measurement signals with respect to each partial spectral region, wherein the or every signal amplifier (9, 34) that is allocated to the partial spectral region amplifies the measuring signal coming from this partial spectral region with a degree of amplification that is allocated to this partial spectral region, and wherein the evaluation unit comprises a summer (10, 34) for summing up the amplified measuring signals.

2. Photometric device in accordance with claim 1, wherein the evaluation unit is an electric circuit and several adjustable control voltage sources, whose respective electric potential controls the degree of amplification of the allocated signal amplifier (9, 34), are available for adjusting the amplification degrees.

3. Photometric device in accordance with claim 1, wherein the evaluation unit is a digital computing device that comprises the summer (10, 34) and means of adjustment with an amplification parameter memory for storing the amplification parameters that are allocated to the respective partial spectral region are incorporated, with the signal amplification being performed with the help of a central processing unit of the computing device by multiplying the measuring signals with the amplification parameters in dependence on the spectral properties of the measuring beam that generates the measuring signal.

4. Photometric device in accordance with claim 3, wherein the spectral unit is an interferometer (22), which comprises a beam splitter (23) for splitting the measuring beam (2) to two optical paths (24, 26), which are limited by a stationary mirror (25) or a moveable mirror (27) that can be moved with a control element (28), with the mirrors (25, 27) being aligned in such a way that the parts of the measuring beam (2) reflecting from them unite in a joint beam path (29) and the means of adjustment, with which amplification degrees can be adjusted, are coupled with the control element (28).

5. Photometric device in accordance with claim 1 wherein a dispersive element (4, 14) is provided as the spectral unit for the spatial splitting of the measuring beam (2) in dependence on its wavelength and the radiation receiver is a detector row (6) with detector elements (7) that are arranged next to each other, with each detector element (7), respectively, being connected with a signal amplifier (9).

6. Photometric device in accordance with claim 5, wherein the dispersive element is a diffraction grating (14).

7. Photometric device in accordance with claim 1, wherein the spectral unit is a spectral switch unit (16) for selecting the partial spectral regions of the measuring beam (2) and a detector element (7) is provided as radiation receiver, with means of adjustment, which are coupled with the spectral switch unit (16) and the detector element (7), being incorporated, with which amplification degrees can be adjusted.

8. Photometric device in accordance with claim 7, wherein the spectral switch unit is a filter wheel (16) with spectral filters that is triggered by a filter wheel drive (17).

9. Photometric device in accordance with claim 1, wherein the radiation source is an infrared radiation source (1) that generates infrared radiation (2) in the medium-range infrared spectral region and the radiation receiver is a sensitive radiation receiver (6, 7) in the medium-range infrared spectral range.

10. Photometric device in accordance with claim 1, wherein the radiation source is an infrared radiation source (1) that generates infrared radiation (2) in the short-range infrared spectral region and the radiation receiver is a sensitive radiation receiver (6, 7) in the short-range infrared spectral range.

11. Photometric device in accordance with claim 1, wherein a spectral accumulator is provided, with which the measuring signals and the partial spectral areas that are allocated to them can be stored in pairs.

12. Method for the photometric determination of the gross calorific value of a test gas comprising the steps of:

propagating a measuring beam into a test cell (3) that is filled with test gas, splitting said measuring beam spectrally into a plurality of adjacent partial spectral regions following propagation through said test cell;

measuring the measuring beam (2) intensities that are permitted to penetrate the test cell (3) using a radiation receiver (6,7), the radiation receiver generating measuring signals in relation to appropriate measuring signals without test gas in the test cell (3) and generating spectral absorption ranges allocated to said partial spectral regions, generating spectral absorption values based upon said measuring signals and respective allocated partial spectral regions, amplifying each spectral absorption value using at least one signal amplifier (9, 34), and wherein the radiation receiver (6, 7), from the composition of the test gas with regard to the components or functional groups and the position of absorption bands and absorption lines, records independent partial spectral regions of an absorption band and/or a spectral region comprising absorption lines, wherein the or every signal amplifier (9, 34) that is allocated to the partial spectral region amplifies the spectral absorption value coming from this partial spectral region with a degree of amplification that is allocated to this partial spectral region, and summing the amplified spectral absorption values to calculate of the gross calorific value of the test gas.

13. Method in accordance with claim 12, wherein the measuring beam (2) is split spatially in dependence on the wavelength.

14. Method in accordance with claim 12, wherein the amplitude of the measuring beam (2) is modulated with the help of an interferometer (22).

15. Method in accordance with claim 12, wherein the spectral absorption values are amplified with allocated partial spectral regions from the spectral range of the C—H oscillation.

16. Method in accordance with claim 15, wherein the spectral absorption values are amplified with allocated partial spectral regions from the spectral range between 3 $\mu$m and 4 $\mu$m.

17. Method in accordance with claim 12, wherein the spectral absorption values are amplified with allocated partial spectral regions from the spectral range of the C—H harmonic oscillation.

18. Method in accordance with claim 17, wherein the spectral absorption values are amplified with allocated partial spectral regions from the spectral range between 1.5 $\mu$m and 2 $\mu$m.

19. Method in accordance with claim 12, wherein the test gas is examined for at least one interfering foreign gas, which does not contribute to the gross calorific value and whose spectral absorption values in dependence on the wavelength are known, by measuring characteristic spectral absorption values at established partial spectral regions, a percentage of the foreign gas in the test gas is determined in dependence on characteristic absorption values and the interfering percentage of the foreign gas is subtracted from the spectral absorption values.

20. Method in accordance with claim 12, wherein the test gas is examined for special gases, which contribute to the gross calorific value and which differ from a main component of the test gas due to their chemical composition or structure, by measuring characteristic spectral absorption values at established wavelengths.

21. Method in accordance with claim 12, wherein the spectral absorption values that are allocated to the partial spectral regions are stored as spectrum in a spectral accumulator.

* * * * *